US006693066B2

(12) United States Patent
Puvvada et al.

(10) Patent No.: US 6,693,066 B2
(45) Date of Patent: Feb. 17, 2004

(54) TOILET BARS CONTAINING SENSORY MODIFIERS COMPRISING CONDITIONING COMPOUND

(75) Inventors: Sudhakar Puvvada, Shelton, CT (US); Michael G. Clarke, Cheshire, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 193 days.

(21) Appl. No.: 10/003,556

(22) Filed: Nov. 15, 2001

(65) Prior Publication Data

US 2003/0104958 A1 Jun. 5, 2003

(51) Int. Cl.[7] .................................................. A61K 7/50

(52) U.S. Cl. ....................... 510/141; 510/152; 510/155; 510/481; 510/499; 510/505

(58) Field of Search ................................. 510/141, 152, 510/155, 481, 499, 505

(56) References Cited

U.S. PATENT DOCUMENTS

| | | | | |
|---|---|---|---|---|
| 4,673,525 | A | | 6/1987 | Small et al. |
| 4,820,447 | A | | 4/1989 | Medcalf, Jr. et al. |
| 4,946,618 | A | | 8/1990 | Knochel et al. |
| 5,264,145 | A | | 11/1993 | French et al. |
| 5,312,559 | A | | 5/1994 | Kacher et al. |
| 5,338,541 | A | | 8/1994 | Matz et al. |
| 5,494,533 | A | | 2/1996 | Woodin, Jr. et al. |
| 5,496,488 | A | | 3/1996 | Kacher et al. |
| 6,001,788 | A | | 12/1999 | Jaworski et al. |
| 6,004,915 | A | | 12/1999 | Elliott et al. |
| 6,057,275 | A | | 5/2000 | Fair et al. |
| 6,066,315 | A | | 5/2000 | Melby et al. |
| 6,107,352 | A | * | 8/2000 | Zofchak et al. ............. 516/914 |
| 6,117,828 | A | | 9/2000 | Puvvada et al. |
| 6,277,798 | B1 | | 8/2001 | Elliott et al. |
| 6,287,578 | B1 | | 9/2001 | Duetsch et al. |

FOREIGN PATENT DOCUMENTS

| | | |
|---|---|---|
| CA | 1051312 | 1/1986 |
| EP | 0 959 094 A1 | 11/1999 |
| WO | 98/14559 | 4/1998 |
| WO | 99/58106 | 11/1999 |

OTHER PUBLICATIONS

*International Search Report PCT/EP 02/11896*, dated Feb. 5, 2003, 3 pp.

* cited by examiner

*Primary Examiner*—Necholus Ogden
(74) *Attorney, Agent, or Firm*—Alan A. Bornstein

(57) ABSTRACT

A toilet bar composition is described that contains an amido tertiary amine, amido amine salt, or amido ammonium skin conditioning agent in an amount effective to enhance skin feel and the deposition of hydrophobic emollients without having a deleterious effect on lathering speed, sand, and slip properties.

21 Claims, No Drawings

TOILET BARS CONTAINING SENSORY MODIFIERS COMPRISING CONDITIONING COMPOUND

BACKGROUND OF THE INVENTION

1. Field of the Invention

The present invention relates to a toilet bar suitable for topical application for cleansing the human body, such as the skin and hair. In particular, it relates to a toilet bar composition producing a high rate and quantity of lather and that conveys excellent sensory properties.

2. The Related Art

Toilet bar skin cleaning properties are well known. An ideal bar composition not only cleans but provides a large quantity of lather and leaves the skin feeling comfortable. To accomplish this, a wide variety of additives have been suggested for inclusion in toilet bars. Some additives enhance the physical properties of the bar such as hardness and wear rate. Other additives enhance the in-use properties such as lather volume, creaminess, lather speed, and stability. Still other additives modify the skin feel both during and after use. Furthermore, consumers often seek a product that meets their specific needs. As a result, a single toilet bar product is not suitable or desirable for every consumer. At the same time, the bar manufacturer desires to reduce costs by minimizing the difference in toilet bar compositions it produces. To these ends, additives that modify the sensory properties at low concentration levels will provide significant advantages to providing varied products to consumers with products that meet the consumer's specific needs and at low cost.

In the past, polymer and high molecular weight additives have typically been used at low levels to modify the sensory properties of cleansing compositions such as shampoos, body washes, shower gels, hand washes. In toilet bars, however, polymer and high molecular weight additives have not been widely used because they frequently have a negative impact on bar feel (sand and grit), lather speed and lather volume. Surprisingly, Applicants have discovered that certain polymeric and low molecular weight amido amines and amido ammonium salts can provide excellent bar feel and lather properties while at the same time providing excellent skin feel when formulated into toilet bars.

U.S. Pat. No. 4,820,447; titled Mild Skin Cleansing Soap Bar With Hydrated Cationic Polymer Skin Conditioner; issued to R. F. Medcalf, Jr., et al. on Apr. 11, 1989 teaches the use of a hydrated cationic polymer in soap bars to improve their mildness. This specific class of polymers has been shown to provide the positive skin feel and mildness without compromising lather, provided that hydration of the polymer is adequate. Similarly, U.S. Pat. No. 4,673,525; titled Ultra Mild Skin Cleansing Composition; issued to L. E. Small, et al. on Jun. 16, 1987 teaches the use of polymeric skin feel additives. They also find that high levels of moisturizer are required. U.S. Pat. No. 4,946,618; titled Toilet Bar Composition Containing Cationic Guar Gum; issued to J. R. Knochel, et al. on Aug. 7, 1990 teaches the use of fast hydrating cationic guar gum (among other polymers) as a way of improving skin feel without enhancing grit. U.S. Pat. No. 5,312,559; titled Personal Cleanser With Moisturizer, issued to M. L. Kacher, et al. on May 17, 1994 teaches the use of various cationic additives in semi-solid compositions with high levels of water (40–70%). U.S. Pat. No. 5,338,541; titled Dual Cationic Terpolymers Providing Superior Conditioning Properties In Hair, Skin And Nail Care Products; issued to G. F. Matz, et al. on Aug. 16, 1994 teaches the use of acrylamide terpolymers having a MW>10,000. U.S. Pat. No. 6,001,788, titled Personal Use Soap Bar Compositions Containing Cationic Polymers, issued to R. J. Jaworski, et al. Feb. 14, 1999 teaches a method of incorporating an unhydrated cationic guar gum in soap bars, and discusses the need for quick hydration. U.S. Pat. No. 6,066,315, titled Ampholyte Polymers For Use In Personal Care Products, issued to A. L. Melby, et al. on May 23, 2000 teaches the use of various specific water soluble ampholytic polymers with high MW (>100,000) for treating keratin that are reportedly superior to previous polymers. U.S. Pat. No. 5,496,488, titled Cleansing Bar Composition Containing Petrolatum Having A Specific Size Range, issued to M. L. Kacher, et al. on Mar. 5, 1996 teaches the use of cationic polymers such as Polyquaternium 10 in bar compositions containing relatively high levels of water (e.g. 10–90% with 28% being exemplified). This patent discloses a method for hydrating polymers with high levels of water and thereby serves to minimize grit. Unfortunately, bars with such high levels of water are disadvantageous. Moreover, none of the above references disclose or suggest the conditioning compounds in the toilet bars of the present invention.

U.S. Pat. No. 6,057,275, titled Bars Comprising Benefit Agent And Cationic Polymer, issued to M. Fair, et al. on May 2, 2000 teaches specific ratios of cationic to surfactant compounds to enhance deposition. The ratios disclosed are in the range of 0.06:1 to 1:1. Conditioning compounds in the present invention are used at significantly lower comparative levels, i.e. in the ratio of conditioning compound to total surfactant compounds of about 0.05:1 to about 0.0001:1; preferably about 0.02:1 to about 0.0001:1. Furthermore, U.S. Pat. No. 6,057,275 discloses that the cationic conditioning compound must be fully hydrated prior to its addition to the bar.

The above mentioned prior art polymers and high molecular weight additives impart a positive moisturized skin feel that consumers appreciate. However, unlike the inventive additives, many of these polymers require substantial hydration and the net result is that such compounds have a negative impact on speed of lather and bar feel properties.

SUMMARY OF THE INVENTION

In one aspect the present invention is a toilet bar, having:

(a) about 0 to about 85% by wt. of a fatty acid soap;

(b) about 0 to about 65% by wt. of a non-soap anionic surfactant;

(c) about 0 to about 25% by wt. of water; and (d) a conditioning compound of the following formula (I)

$$R_1C(O)NH—R_2—B(M) \quad (I)$$

in which $R_1C(O)NH—$ is a C6 to C22 alkyl amide radical, a C6 to C22 alkenyl amide radical, a C3 to C22 alkoxyl amide radical, or a C6 to C22 alkylaryl amide radical; either substituted or unsubstituted;

$R_2$ is a linking group selected from, a C1 to C10 alkyl group, a C3 to C10 alkenyl group, a C3 to C22 alkoxyl group, or a C6 to C22 alkylaryl group; either substituted or unsubstituted;

B is an amine or ammonium radical selected from the group of secondary alkyl amines or ammonium salts, secondary alkenyl amines or ammonium salts, secondary alkoxyl amines or ammonium salts, secondary alkanolamines or ammonium salts, secondary alkylaryl amines or ammonium salts, secondary cyclic amines or ammonium salts, heterocyclic amines or ammonium salts, and M is an anion when B is an ammonium radical.

DETAILED DESCRIPTION OF THE INVENTION

In one aspect of the invention is a toilet bar, comprising:

(a) about 0 to about 85% by wt., preferably about 10 to about 80% by wt. of a fatty acid soap;

(b) about 0 to about 65% by wt., preferably about 5 to about 55% by wt. of a non-soap anionic surfactant;

(c) about 0 to about 25% by wt., preferably about 3 to about 20% by wt. of water; and (d) a conditioning compound of the following formula (I)

$$R_1C(O)NH—R_2—B(M) \quad (I)$$

in which:

$R_1C(O)NH—$ is a C6 to C22 alkyl amide radical, a C6 to C22 alkenyl amide radical, a C3 to C22 alkoxyl amide radical, or a C6 to C22 alkylaryl amide radical; either substituted or unsubstituted;

$R_2$ is a linking group selected from, a C1 to C10 alkyl group, a C3 to C10 alkenyl group, a C3 to C22 alkoxyl group, or a C6 to C22 alkylaryl group; either substituted or unsubstituted;

B is an amine or ammonium radical selected from the group of secondary alkyl amines or ammonium salts, secondary alkenyl amines or ammonium salts, secondary alkoxyl amines or ammonium salts, secondary alkanolamines or ammonium salts, secondary alkylaryl amines or ammonium salts, secondary cyclic amines or ammonium salts, heterocyclic amines or ammonium salts, preferably dimethyl amine, dimethyl ammonium, morpholine, and morpholinium; and M is an anion when B is an ammonium radical.

Preferably the sum of the fatty acid soap (a) and the non-soap anionic surfactant (b) is in the concentration range of about 20 to about 85 wt. %. Advantageously the conditioning compound is present at a level greater than about 0.001 wt. %, preferably greater than about 0.01 wt. %. More preferably the conditioning compound is present in the concentration range of about 0.01 to about 3 wt. %, still more preferably in the concentration range of about 0.01 to about 1 wt. %; and most preferably in the concentration range of about 0.01 to about 0.5 wt. %. Preferably conditioning compounds in the present invention are used in the ratio of conditioning compound to total surfactant compounds of about 0.05:1 to about 0.0001:1; preferably about 0.02:1 to about 0.0001:1.

Advantageously, the $R_1C(O)NH—$ amide radical is selected from cocamido, ricinoleamido, stearamido, isostearamido, oleamido, behenamido, wheat germ amido, lauramido, soyamido, octamido, sunflower seed amido, and the like; the $R_2$ linking group is C2 to C6 alkyl or alkoxyl, and the like; preferably C3 alkyl, and the M anion is selected from hydrolyzed protein, propionate, lactate and the like. Preferably the $R_1C(O)NH—$ amide radical does not include acrylamido or acrylic acid amido radicals.

When B is an ammonium radical and a hydrolyzed protein containing conditioning agent is used, the hydrolyzed protein is advantageously selected from collagen, silk protein, keratin, wheat protein, soy protein, milk protein and the like.

Advantageously, the inventive toilet bar further comprises a hydrophobic emollient in a concentration greater than about 0.5 wt. %, preferably greater than about 4 wt. %. Preferably the hydrophobic emollient is present in a concentration range of about 1 to about 45 wt. %, more preferably about 5 to about 30 wt. %. Preferably the hydrophobic emollient is selected from a C12 to C18 fatty acid, a triglyceride oil, a petrolatum or mineral oil, or a combination thereof, and the like. Preferably the inventive bar deposits greater than about 0.01 micrograms/cm2, preferably about 0.1 micrograms/cm2 of the hydrophobic emollient to the surface of the skin or hair.

The inventive bar has excellent bar feel and lathering properties. Preferably, the inventive bar has a sand rating no greater than the sand rating of a bar having the same formulation except without the conditioning compound. Similarly, the inventive bar preferably has a slip rating no greater than the slip rating of a bar having the same formulation except without the conditioning compound. In addition, the inventive bar preferably has a lather volume at least as great as the lather volume of a bar having the same formulation except without the conditioning compound.

In another aspect, the present invention is a toilet bar, having:

(a) about 0 to about 30% by wt.; preferably about 0 to about 20% by wt.; and more preferably about 0 to about 15% by wt. of a fatty acid soap;

(b) about 15 to about 60%; preferably about 20 to about 55%; and more preferably about 25 to about 50% by wt. of a non-soap anionic surfactant; and (c) a conditioning compound of the formula (I).

Preferably this aspect of the inventive bar contains an amount of free water less than about 12% by wt., preferably less than about 10% by wt. and most preferably less than about 7% by wt. Free water is herein defined as that quantity of water present in the bar which is able to solvate acidic compounds. This ability is in contrast to bound water, such as the water of crystallization of unsolvated materials, whereby the bound water is unable to solvate acidic materials to the same extent that free water can.

In another aspect of the present invention is a toilet bar, having (a) about 30 to about 80% by wt.; preferably about 40 to about 70% by wt.; more preferably about 50% to about 60% by wt. of a fatty acid soap;

(b) about 5 to about 40% by wt.; preferably about 7 to about 30%; more preferably about 10 to about 20% by wt. of a non-soap anionic surfactant; and (c) a conditioning compound of the formula (I).

Preferably this embodiment of the inventive bar contains an amount of free water less than about 25% by wt., preferably less than about 20% by wt. and most preferably less than about 15% by wt.

In a further aspect of the present invention, is a toilet bar, having (a) about 40 to about 85% by wt.; preferably about 50 to about 80% by wt.; more preferably about 60 to about 75% by wt. of a fatty acid soap;

(b) about 0 to about 10% by wt.; preferably about 0 to about 7% by wt.; more preferably about 0 to about 5% by wt. of a non-soap anionic surfactant; and (c) a conditioning compound of the formula (I).

In a preferred embodiment of this aspect of the invention, there is more than about 0.1% by wt. of a non-soap anionic surfactant; preferably more than about 0.5% by wt.; and more preferably more than about 1.0% by wt.

Preferably this embodiment of the inventive bar contains an amount of free water in the range of about 5 to about 30% by wt., preferably in the range of about 7 to about 25% by wt, and most preferably in the range of about 10 to about 20% by wt.

Surfactants:

Surfactants are an essential component of the inventive toilet bar composition. They are compounds that have hydrophobic and hydrophilic portions that act to reduce the surface tension of the aqueous solutions they are dissolved in. Useful surfactants can include anionic, nonionic, amphoteric, and cationic surfactants, and blends thereof.

Anionic Surfactants:

Soaps.

The inventive toilet bar may contain soap, preferably it contains at least 0.1% by wt. of soap. The term "soap" is used herein in its popular sense, i.e., the alkali metal or alkanol ammonium salts of alkane- or alkene monocarboxylic acids. Sodium, potassium, mono-, di- and tri-ethanol ammonium cations, or combinations thereof, are suitable for purposes of this invention. In general, sodium soaps are used in the compositions of this invention, but from about 1% to about 25% of the soap may be ammonium, potassium, magnesium, calcium or a mixture of these soaps. The soaps useful herein are the well known alkali metal salts of alkanoic or alkenoic acids having about 12 to 22 carbon atoms, preferably about 12 to about 18 carbon atoms. They may also be described as alkali metal carboxylates of alkyl or alkene hydrocarbons having about 12 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of tallow, and vegetable oil. More preferably the vegetable oil is selected from the group consisiting of palm oil, coconut oil, palm kernal oil, palm stearin, and hydrogenated rice bran oil, or mixtures thereof, since these are among the more readily available fats. Especially preferred is coconut oil. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are C16 and higher. Preferred soap for use in the compositions of this invention has at least about 85% fatty acids having about 12–18 carbon atoms.

Coconut oil employed for the soap may be substituted in whole or in part by other "high-lauric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 15% to about 20% coconut oil and about 80% to about 85% tallow. These mixtures contain about 95% fatty acids having about 12 to about 18 carbon atoms. As mentioned above, the soap may preferably be prepared from coconut oil, in which case the fatty acid content is about 85% of $C_{12}$–$C_{18}$ chain length.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

Skin Conditioning Compounds

An essential component in compositions according to the invention is a compound of formula (I), such as an amido tertiary amine, an amido amine salt, an amido quaternary ammonium compound, or a combination thereof. Useful compounds include cocamidopropyl dimethylamine, cocamidopropyl diethylamine, cocamidopropyl diisopropylamine, cocamidopropyl diphenylamine, cocamidopropyl morpholine, cocamidopropyl piperazine, ricinoleamidopropyl dimethylamine, ricinoleamidopropyl diethylamine, ricinoleamidopropyl diisopropylamine, ricinoleamidopropyl diphenylamine, ricinoleamidopropyl morpholine, ricinoleamidopropyl piperazine, stearamido dimethylamine, stearamido diethylamine, stearamido diisopropylamine, stearamido diphenylamine, stearamido morpholine, stearamido piperazine, isostearamido dimethylamine, isostearamido diethylamine, isostearamido diisopropylamine, isostearamido diphenylamine, isostearamido morpholine, isostearamido piperazine, oleamido dimethylamine, oleamido diethylamine, oleamido diisopropylamine, oleamido diphenylamine, oleamido morpholine, oleamido piperazine, behenamido dimethylamine, behenamido diethylamine, behenamido diisopropylamine, behenamido diphenylamine, behenamido morpholine, behenamido piperazine, wheat germ amido dimethylamine, wheat germ amido diethylamine, wheat germ amido diisopropylamine, wheat germ amido diphenylamine, wheat germ amido morpholine, wheat germ amido piperazine, lauramido dimethylamine, lauramido diethylamine, lauramido diisopropylamine, lauramido diphenylamine, lauramido morpholine, lauramido piperazine, soyamido dimethylamine, soyamido diethylamine, soyamido diisopropylamine, soyamido diphenylamine, soyamido morpholine, soyamido piperazine, octamido dimethylamine, octamido diethylamine, octamido diisopropylamine, octamido diphenylamine, octamido morpholine, octamido piperazine, and sunflower seed amido dimethylamine, sunflower seed amido diethylamine, sunflower seed amido diisopropylamine, sunflower seed amido diphenylamine, sunflower seed amido morpholine, sunflower seed amido piperazine; their corresponding quaternary ammonium propionate and lactate salts, and their corresponding quaternary ammonium hydrolyzates of silk or wheat protein, and the like. Many of these compounds can be obtained as the Mackine™ Amido Functional Amines, Mackalene™ Amido functional Tertiary Amine Salts, and Mackpro® cationic protein hydrolysates from the McIntyre Group Ltd. (University Park, Ill.).

In a preferred embodiment of the invention having a hydrolyzed protein conditioning agent, the average molecular weight of the hydrolyzed protein is preferably about 2500. Preferably 90% of the hydrolyzed protein is between a molecular weight of about 1500 to about 3500. In a preferred embodiment, MACKPRO™ WWP (i.e. wheat germ amido dimethylamine hydrolyzed wheat protein) is added at a concentration of 0.1% (as is) in the bar. This results in a MACKPRO™ WWP "solids" of 0.035% in the final bar formula for this embodiment.

Superfatting Agent

Free fatty acid, as a superfatting agent may be added to the composition according to the present invention at a level of 2–10% on total actives. This level of free fatty acids can be obtained by the addition of free fatty acids per se or by the addition of a non-fatty acid superfatting agent which protonates a portion of the fatty acid soaps present to form the free fatty acid. Suitable fatty acid superfatting agents include tallow, coconut, palm and palm-kernel fatty acids. Other fatty acids can be employed although the low melting point fatty acids, particularly the laurics, are preferred for ease of processing. Preferred levels of fatty acid are about 3 to about 8 wt. %, most preferably about 5 wt. % based on total actives.

Synthetic Anionic Surfactants

The cleansing composition of the present invention may contain one or more non-soap anionic detergents. The anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates, and the like.

Sulfosuccinates may be monoalkyl sulfosuccinates having the formula:

$R^4O_2CCH_2CH(SO_3M)CO_2M$; and amide-MEA sulfosuccinates of the formula;

$$R^4CONHCH_2CH_2O_2CCH_2CH(SO_3M)CO_2M$$

wherein $R^4$ ranges from $C_8$–$C_{22}$ alkyl and M is a solubilizing cation.

Sarcosinates are generally indicated by the formula:

$R^1CON(CH_3)CH_2CO_2M$, wherein $R^1$ ranges from $C_8$–$C_{20}$ alkyl and M is a solubilizing cation.

Taurates are generally identified by formula:

$$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

The inventive toilet bar composition preferably contains non-soap anionic surfactants, preferably $C_8$–$C_{14}$ acyl isethionates. These esters are prepared by reaction between alkali metal isethionate with mixed aliphatic fatty acids having from 6 to 12 carbon atoms and an iodine value of less than 20.

The acyl isethionate may be an alkoxylated isethionate such as is described in llardi et al., U.S. Pat. No. 5,393,466, titled "Fatty Acid Esters of Polyalkoxylated isethonic acid; issued Feb. 28, 1995; hereby incorporated by reference. This compound has the general formula:

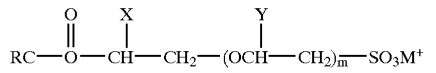

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

In another embodiment of the inventive toilet bar, there is less than 5% by wt. of any of the following anionic surfactants: alkyl sulfates, alkyl sulfonates, alkyl benzene sulfonates, alkyl alkoxy sulfates, acyl taurides, acyl sulfates, and polyhydfroxy fatty acid amides either individually or of a blend thereof.

Preferably there is less than 1%, and more preferably less than 0.1% by wt. of these surfactants Amphoteric Surfactants One or more amphoteric surfactants may be used in this invention. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

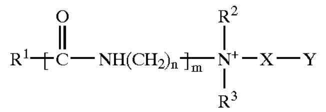

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $—CO_2—$ or $—SO_3—$

Suitable amphoteric surfactants within the above general formula include simple betaines of formula:

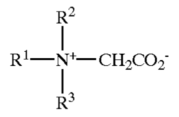

and amido betaines of formula:

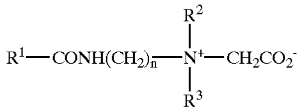

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

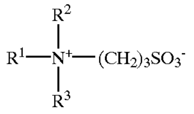

or

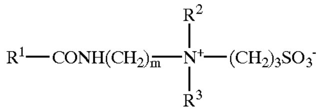

where m is 2 or 3, or variants of these in which $-(CH_2)_3SO_3^-$ is replaced by

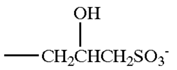

In these formulae $R^1$, $R^2$ and $R^3$ are as discussed previously.

Amphoacetates and diamphoacetates are also intended to be covered in possible zwitterionic and/or amphoteric compounds which may be used such as e.g., sodium lauroamphoacetate, sodium cocoamphoacetate, and blends thereof, and the like.

Nonionic Surfactants

One or more nonionic surfactants may also be used in the toilet bar composition of the present invention.

The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$–$C_{22}$) phenols ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Cationic Surfactants

One or more cationic surfactants may also be used in the inventive toilet bar composition.

Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar. 27, 1973; and "Surface Active Agents and Detergents" (Vol. I & II) by Schwartz, Perry & Berch, both of which are also incorporated into the subject application by reference.

Optional Ingredients

In addition, the inventive toilet bar composition of the invention may include 0 to 15% by wt. optional ingredients as follows:

perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer) and the like; all of which are useful in enhancing the appearance or cosmetic properties of the product.

The compositions may further comprise antimicrobials such as 2-hydroxy-4,2', 4' trichlorodiphenylether (DP300); preservatives such as dimethyloldimethylhydantoin (Glydant XL1000), parabens, sorbic acid etc., and the like.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and the like may be used advantageously in amounts of about 0.01% or higher if appropriate.

Humectants and Emollients

Humectants such as polyhydric alcohols, e.g. glycerine and propylene glycol, and the like; and polyols such as the polyethylene glycols listed below and the like may be used.

| | |
|---|---|
| Polyox WSR-205 | PEG 14M, |
| Polyox WSR-N-60K | PEG 45M, or |
| Polyox WSR-N-750 | PEG 7M. |

Emollients may be advantageously used in the present invention. The emollient "composition" may be a single benefit agent component or it may be a mixture of two or more compounds one or all of which may have a beneficial aspect. In addition, the benefit agent itself may act as a carrier for other components one may wish to add to the inventive toilet bar.

Hydrophobic emollients, hydrophilic emollients, or a blend thereof may be used. Preferably, hydrophobic emollients are used in excess of hydrophilic emollients in the inventive toilet bar composition. Most preferably one or more hydrophobic emollients are used alone. Hydrophobic emollients are preferably present in a concentration greater than about 0.5% by weight, more preferably about 4% by weight. The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content.

Useful emollients include the following:

(a) silicone oils and modifications thereof such as linear and cyclic polydimethylsiloxanes; amino, alkyl, alkylaryl, and aryl silicone oils;

(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic and hydrophillic plant extracts;

(e) hydrocarbons such as liquid paraffins, Vaseline®, microcrystalline wax, ceresin, squalene, pristan and mineral oil;

(f) higher fatty acids such as lauric, myristic, palmitic, stearic, behenic, oleic, linoleic, linolenic, lanolic, isostearic, arachidonic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and pseudo-ceramides as described in European Patent Specification No. 556,957;

(k) vitamins, minerals, and skin nutrients such as milk, vitamins A, E, and K; vitamin alkyl esters, including vitamin C alkyl esters; magnesium, calcium, copper, zinc and other metallic components;

(l) sunscreens such as octyl methoxyl cinnamate (Parsol MCX) and butyl methoxy benzoylmethane (Parsol 1789);

(m) phospholipids;

(n) antiaging compounds such as alpha hydroxy acids, beta hydroxy acids; and (o) mixtures of any of the foregoing components, and the like.

Preferred emollient benefit agents are selected from C12 to C18 fatty acids, triglyceride oils, mineral oils, petrolatum, and mixtures thereof.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated. Physical test methods are described below:

EXAMPLE 1

Lather and Bar Feel Properties of Toilet Bars

The lather volume and bar feel properties of inventive and comparative toilet bars formulated with various conditioning compounds according to table 1 were assessed and the results are illustrated in table 3. Bar feel properties were determined by assessing the sand and slip ratings of the respective bars as provided below.

It was observed that that the inventive toilet bars formulated with cationic additives according to formula (I) enhance lather without negatively impacting sand and slip bar feel properties. Although not wishing to be bound by theory, it is believed that certain prior art cationic additives hydrate very slowly, and therefore often lead to negative toilet bar properties such as drag and sand. In some embodiments, the inventive conditioning compounds hydrate faster and as a result do not impact on drag and slip. The two comparative conditioning compounds illustrated in table 1 (i.e. Jaguar C13S & Mackpro NLW) show an increase in sand and reduction in slip which the typical consumer does not prefer in a moisturizing bar. Furthermore, the formulation with Jaguar C13S shows a minimal increase in lather probably because it is not substantially hydrated.

TABLE 1

Base formulation A used for bar properties study

| Component | Wt. % |
|---|---|
| Soap (blend composition) | 55 (20 coco, 35 tallow) |
| Sodium cocyl isethionate | 20 |
| Fatty Acids (C10 to C18) | 7 |
| Fragrance | 1.3 |
| Sodium isethionate + sodium chloride | 6 |
| Total Water | About 12 |

TABLE 2

Base formulation B used for deposition study

| Component | Wt. % |
|---|---|
| Soap (blend composition) | 55 (16 coco, 39 tallow) |
| Sodium cocyl isethionate | 20 |
| Fatty Acids (C10 to C18) | 7 |
| Cocoamidopropyl betaine | 0 |
| Fragrance | 1.3 |
| Triglyceride oil | 0.5 |
| Sodium isethionate + sodium chloride | 6 |
| Total Water | About 12 |

Method of Bar Production:

The bar compositions used in the examples herein were formulated by blending all ingredients except the conditioning agent and fragrance for about 30–40 minutes at temperatures of 180–230 F. The batch is then cooled and solidified in a spray dryer or a chill roll. The chips are then mixed with fragrance and the conditioning agent and optionally triglyceride oil is blended in a chip mixer for about 5–10 minutes. This is followed by extrusion and stamping into a bar.

TABLE 3

Lather & Bar Property Data

| Conditioning compound (at 0.25% active) added to Base formulation A | Category | Lather Volume (mls) | Sand Rating | Slip Rating |
|---|---|---|---|---|
| Control (No additive) | Comparative | 110, 125, 140 (Mean = 125) | 1 | 1 |
| Wheatgerm amidopropyl Dimethylamine Hydrolyzed wheat protein (Mackpro ™ WWP) | Inventive | 130, 140, 130 (Mean = 145) | 1 | 1 |
| Isostearamidopropyl Morpholine Hydrolyzed silk protein (Mackpro ™ ISP) | Inventive | 135, 150, 160 (Mean = 148) | 1 | 1 |
| Guar Hydroxypropyl trimonium chloride (Jaguar ™ C13S) | Comparative | 130, 140, 130 (Mean = 133) | 3 | 2 |
| Wheatgerm amidopropyl Dimethylamine (Mackine ™ 701) | Inventive | 130, 145, 160 (Mean = 145) | 1 | 1 |
| Quaternium 79 Hydrolyzed wheat protein (Mackpro ™ NLW) | Comparative | 130, 160, 150 (Mean = 146) | 2 | 2 |

EXAMPLE 2

Skin Deposition Properties

The skin deposition properties of emollients contained in inventive and comparative toilet bars formulated with and without an inventive conditioning compound according to table 2 were assessed and the results are illustrated in table 5. The method for determining skin deposition is provided below. The incorporation of the inventive additive at a very low level (i.e. about 0.03%) enhances emollient deposition significantly.

TABLE 5

Deposition Data

| Conditioning compound (at 0.03% active added to Base formulation A) | Category | Mean Fatty acid deposition (micro g/sq. cm) |
|---|---|---|
| Control | Comparative | −0.19 |
| Wheatgerm amidopropyl Dimethylamine Hydrolyzed wheat protein (Mackpro WWP) | Inventive | 0.32 |

Description of Test Methods:

Skin Deposition Method

The test included 11 subjects using a toilet bar with the inventive conditioning agent, i.e. Mackpro WWP, on both arms and 9 subjects using a comparative bar without an inventive conditioning agent on both arms.

Prior to the washing phase of the test, the panelists used Ivory® soap daily on one arm to induce dry skin (dry-down period). The other arm of each panelist was regarded as normal (not dry) skin. Panelists were instructed not to apply skin creams or lotions to their arms during this period.

After the dry-down period, panelists washed both arms once with Ivory® soap. After this pre-wash, a skin site on each forearm was extracted using the standard lipid extraction procedure (baseline extraction) as provided below. This provided samples to determine baseline extracted stearic acid values. The purpose of the pre-wash was to remove any soil, sweat, sebum, etc. in order to provide a uniform substrate for examination for wash deposition.

After the baseline extraction, each arm of each panelist was washed with the test bar (same bar on each arm as stated above) using a standard wash and rinse procedure as described below. After rinsing, arms were patted dry with a paper towel and extracted using the standard lipid extraction procedure. Extraction samples were analyzed for stearic acid content.

The standard lipid extraction procedure used was as follows:

An open-ended cylinder (3-cm in diameter) was held tightly against the test site. A measured amount of (2 mls) of solvent (1:1 Isopropanol:acetone mixture) was placed in the cylinder. The solvent was gently agitated by the glass pipette for 1 minute. After 1 minute, the solvent was removed from the cylinder with the pipette and the extraction procedure was repeated for a total time of 2 minutes yielding 4 mls. of total extract.

The standard wash and rinse procedure used was as follows:

1. Wet inner forearm of subject.
2. Wet bar.
3. Rotate bar in hand 10 times to generate lather.
4. With lather in gloved hand wash test site for 30 seconds.
5. Rinse for 15 seconds.
6. Gently pat dry.

Sand/Slip Rating Method:

All bars were washed with by panelists for one minute (under running water at approx. 85 F). Then each bar was washed with for 10 rotations under running water at approx. 85F. The bars were then removed from the running water and evaluated for sand and slip by rotating in hand according to the following criteria. The number of particles refers to the total number of hard, distinct particles felt by the user over the entire bar. The area of (bar) face with pumice feel refers to the area of general roughness (apart from distinct hard particles) over a single face of the bar.

| Sand # of particles | Rating | Slip Area of face with pumice feel | Rating |
|---|---|---|---|
| 0 | 1 | None | 1 |
| 1–2 | 2 | Very small amount | 2 |
| 3–4 | 3 | About ¼ of one face | 3 |
| 5–6 | 4 | ¼–½ of one face | 4 |
| 7+ | 5 | Over ½ of one face | 5 |

Lather Volume Measurement Procedure:

Apparatus

Two large sinks and a measuring funnel were used. The measuring funnel is fabricated using a 10.5-inch diameter plastic funnel and a 300 ml graduated cylinder with the bottom cleanly removed. The cylinder is fitted with the 0 ml mark over the funnel stem. The cylinder is sealed onto the funnel.

Procedure a) Place the funnel at the bottom of the Sink #1. Add tap water to the sink until the 0 ml mark of the funnel is reached.

b) Generate lather.

1) Run tap on sink #2.
2) Set temperature at 85 F.
3) Holding the bar between both hands under running water, rotate the bar for 10 half turns.
4) Remove hands and bar from under the running water.
5) Rotate the bar 15 half turns.
6) Lay the bar aside.
7) Work up the lather for 10 seconds.
8) Place funnel over hands.
9) Lower hands and funnel into Sink #1.
10) When hands are fully immersed, slide from under the funnel.
11) Lower funnel to the bottom of the sink.
12) Read the lather volume.
13) Remove the funnel from Sink #1.
14) Rinse funnel and hands in sink #2.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A toilet bar, comprising:

(a) about 0 to about 85% by wt. of a fatty acid soap;

(b) about 0 to about 65% by wt. of a non-soap anionic surfactant;

(c) about 0 to about 25% by wt. of water;

(d) a conditioning compound of the following formula (I)

$$R_1C(O)NH—R_2—B(M) \quad (I)$$

in which:

$R_1C(O)NH$— is a C6 to C22 alkyl amide radical, a C6 to C22 alkenyl amide radical, an alkoxyl amide radical, or an alkylaryl amide radical; either substituted or unsubstituted $R_2$ is a linking group selected from a C1 to C10 alkyl group, a C3 to C10 alkenyl group, an alkoxyl group, or an alkylaryl group; either substituted or unsubstituted;

B is an amine or ammonium radical selected from the group of secondary alkyl amines or their ammonium salts, secondary alkenyl amines or their ammonium salts, secondary alkoxyl amines or their ammonium salts, secondary alkanolamines or their ammonium salts, secondary alkylaryl amines or their ammonium salts, secondary cyclic amines or their ammonium salts, heterocyclic amines or their ammonium salts, and M is an anion when B is an ammonium radical.

(e) greater than about 0.5% wt. % of a hydrophobic emollient; and wherein the sum of the fatty acid soap (a) and the non-soap surfactant (b) is in the concentration range of about 20 to about 85 wt. %.

2. The toilet bar of claim 1, wherein the concentration of fatty acid soap is about 10 to about 80% by wt.; the concentration of non-soap anionic surfactant is about 5 to about 55% by wt.; and the concentration of water is about 3 to about 20% by wt.

3. The toilet bar of claim 1, wherein B is selected from dimethyl amine, dimethyl ammonium, morpholine, and morpholinium.

4. The toilet bar of claim 1 wherein the conditioning compound is present at a level greater than about 0.001 wt. %.

5. The toilet bar of claim 1 wherein the conditioning compound is present at a level than about 0.01 wt. %.

6. The toilet bar of claim 1 wherein the conditioning compound is present in the concentration range of about 0.01 to about 3 wt. %.

7. The toilet bar of claim 1 wherein the conditioning compound is present in the concentration range of about 0.01 to about 1 wt. %.

8. The toilet bar of claim 1 wherein the conditioning compound is present in the concentration range of about 0.01 to about 0.5 wt. %.

9. The toilet bar of claim 1 wherein $R_1C(O)NH$— amide radical is selected from cocamido, ricinoleamido, stearamido, isostearamido, oleamido, behenamido, wheat germ amido, lauramido, soyamido, octamido, and sunflower seed amido.

10. The toilet bar of claim 1 wherein the $R_2$ linking group is C2 to C6 alkyl or alkoxyl, either substituted or unsubstituted.

11. The toilet bar of claim 1 wherein the M anion is selected from hydrolyzed protein, propionate, and lactate.

12. The toilet bar of claim 11 wherein the hydrolyzed protein is selected from collagen, silk protein, keratin, wheat protein, soy protein, and milk protein.

13. The toilet bar of claim 1 wherein the hydrophobic emollient is in a concentration greater than about 4 wt. %.

14. The toilet bar of claim 1 wherein the hydrophobic emollient is in a concentration range of about 1 to about 45 wt. %.

15. The toilet bar of claim 1 further comprising a hydrophobic emollient in a concentration range of about 5 to about 30 wt. %.

16. The toilet bar of claim 1 wherein the bar deposits greater than about 0.01 micrograms/cm2 of the hydrophobic emollient to the surface of the skin or hair.

17. The toilet bar of claim 1 wherein the bar deposits greater than about 0.1 micrograms/cm2 of the hydrophobic emollient to the surface of the skin or hair.

18. The toilet bar of claim 1 wherein the bar has a sand rating no greater than the sand rating of a bar having the same formulation except without the conditioning compound.

19. The toilet bar of claim 1 wherein the bar has a slip rating no greater than the slip rating of a bar having the same formulation except without the conditioning compound.

20. The toilet bar of claim 1 wherein the bar has a lather volume not less than the lather volume of a bar having the same formulation except without the conditioning compound.

21. The toilet bar of claim 1 wherein the hydrophobic emollient is selected from a C12 to C18 fatty acid, a triglyceride oil, petrolatum or mineral oil, or a blend thereof.

* * * * *